(12) United States Patent
Tai et al.

(10) Patent No.: US 11,246,543 B2
(45) Date of Patent: Feb. 15, 2022

(54) SYSTEMS AND METHODS FOR POINT-OF-CARE POSITRON EMISSION TOMOGRAPHY

(71) Applicant: WASHINGTON UNIVERSITY, St. Louis, MO (US)

(72) Inventors: Yuan-Chuan Tai, St. Louis, MO (US); Jie Wen, St. Louis, MO (US); Ke Li, St. Louis, MO (US); Aswin John Mathews, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 15/524,699

(22) PCT Filed: Nov. 12, 2015

(86) PCT No.: PCT/US2015/060332
§ 371 (c)(1),
(2) Date: May 5, 2017

(87) PCT Pub. No.: WO2016/077554
PCT Pub. Date: May 19, 2016

(65) Prior Publication Data
US 2017/0332983 A1 Nov. 23, 2017

Related U.S. Application Data

(60) Provisional application No. 62/078,783, filed on Nov. 12, 2014.

(51) Int. Cl.
*G06K 9/00* (2006.01)
*A61B 6/03* (2006.01)
(Continued)

(52) U.S. Cl.
CPC ............ *A61B 6/037* (2013.01); *G01T 1/2985* (2013.01); *G06T 11/003* (2013.01); *A61B 5/0022* (2013.01); *A61B 6/025* (2013.01)

(58) Field of Classification Search
CPC ......... A61B 5/055; A61B 6/032; A61B 6/503; A61B 6/504; A61B 6/506; A61B 6/5241;
(Continued)

(56) References Cited

U.S. PATENT DOCUMENTS 6,539,074 B1 *  3/2003  Yavuz ................... A61B 6/032
                                                378/4
6,727,502 B1 *  4/2004  Matthews ............. G01T 1/1644
                                             250/363.02
(Continued)

OTHER PUBLICATIONS

International Search Report and Written Opinion for International Application No. PCT/US2015/060332, dated Feb. 11, 2016, 7 pages.

*Primary Examiner* — Avinash Yentrapati
(74) *Attorney, Agent, or Firm* — Armstrong Teasdale LLP

(57) ABSTRACT

A positron emission tomography (PET) system is provided. The system includes a first detector panel including a first array of detectors, a second detector panel including a second array of detectors, said second detector panel being moveable relative to a point between the first detector panel and the second detector panel, a tracking system configured to detect a position of said second detector panel relative to the first detector panel while imaging a subject, a computing device in communication with the first detector panel, the second detector panel, and the tracking system, the computing device configured to receive coincidence data from the first and second detector panels, receive position data from the tracking system, wherein each coincidence datum of the received coincidence data is associated with a unique position datum of the received position data, and reconstruct a (Continued)

plurality of images based on the received coincidence data and the received position data.

20 Claims, 15 Drawing Sheets

(51) Int. Cl.
  *G01T 1/29*  (2006.01)
  *G06T 11/00* (2006.01)
  *A61B 5/00*  (2006.01)
  *A61B 6/02*  (2006.01)

(58) Field of Classification Search
  CPC ..... A61B 6/5264; A61B 6/5288; A61B 8/085; A61B 8/0883; A61B 8/0891; A61B 8/463; A61B 8/467; A61B 8/483; A61B 8/488; A61B 8/5207; A61B 8/5253; A61B 8/5276; A61B 8/5284; A61B 6/037; A61B 5/0022; A61B 6/025; G01R 33/5608; G01R 33/5673; G06T 11/008; G06T 2207/20212; G06T 2207/30048; G06T 3/4038; G06T 1/2985; G06T 11/003
  See application file for complete search history.

(56) References Cited

U.S. PATENT DOCUMENTS

| | | | | |
|---|---|---|---|---|
| 7,365,334 | B1* | 4/2008 | Gordon | A61B 5/1127 |
| | | | | 250/363.04 |
| 7,750,311 | B2* | 7/2010 | Daghighian | A61B 8/0841 |
| | | | | 250/398 |
| 8,664,611 | B2 | 3/2014 | Xie et al. | |
| 2003/0128801 | A1* | 7/2003 | Eisenberg | A61B 6/032 |
| | | | | 378/19 |
| 2004/0004188 | A1* | 1/2004 | Tai | G01T 1/2985 |
| | | | | 250/363.03 |
| 2007/0127789 | A1* | 6/2007 | Hoppel | A61B 6/5247 |
| | | | | 382/128 |
| 2007/0167749 | A1* | 7/2007 | Yarnall | A61B 90/39 |
| | | | | 600/431 |
| 2007/0274456 | A1* | 11/2007 | Holt | G01N 23/046 |
| | | | | 378/207 |
| 2008/0230704 | A1* | 9/2008 | Daghighian | A61B 8/0841 |
| | | | | 250/363.03 |
| 2010/0280364 | A1* | 11/2010 | Lu | G06T 19/00 |
| | | | | 600/424 |
| 2011/0211665 | A1* | 9/2011 | Maurer, Jr | A61B 6/4435 |
| | | | | 378/9 |
| 2012/0068076 | A1* | 3/2012 | Daghighian | A61B 6/037 |
| | | | | 250/363.03 |
| 2013/0087697 | A1* | 4/2013 | Xie | A61B 6/488 |
| | | | | 250/252.1 |
| 2015/0069257 | A1* | 3/2015 | Besson | A61B 6/463 |
| | | | | 250/394 |
| 2015/0085970 | A1* | 3/2015 | Bouhnik | A61B 6/032 |
| | | | | 378/5 |
| 2015/0327831 | A1* | 11/2015 | Levin | A61B 6/037 |
| | | | | 600/427 |
| 2016/0242682 | A1* | 8/2016 | Gulati | A61B 5/6801 |
| 2017/0332983 | A1* | 11/2017 | Tai | A61B 6/037 |
| 2018/0200539 | A1* | 7/2018 | Amato | G21K 5/04 |

* cited by examiner

900

SYSTEMS AND METHODS FOR POINT-OF-CARE POSITRON EMISSION TOMOGRAPHY

CROSS-REFERENCE TO RELATED APPLICATION(S)

This application claims the benefit of priority to U.S. Provisional Patent Application No. 62/078,783, filed Nov. 12, 2014, the entire disclosure of which is incorporated herein by reference.

STATEMENT REGARDING FEDERALLY SPONSORED RESEARCH & DEVELOPMENT

This invention was made with government support under CA136554 awarded by the National Institutes of Health; DE-SC0005157 awarded by the Department of Energy; and DBI1040498 awarded by the National Science Foundation. The government has certain rights in the invention.

BACKGROUND OF THE DISCLOSURE

The exemplary embodiments generally relate to positron emission tomography (PET) systems and, more specifically, to a PET system enabling molecular imaging in point-of-care settings. This new class of PET systems is referred to herein as point-of-care PET (PoC-PET).

Positron emission tomography (PET) provides measurement of the spatial and temporal distribution of molecules (e.g., ligands) that are labeled with positron-emitting radio-nuclides. Typical PET scanners use coincidence detection to provide electronic collimation of annihilation γ-rays that are generated when positrons annihilate with electrons. As an example, PET is widely used for investigating cancer, neuropsychiatric diseases such as Alzheimer's and Dementia, cardiovascular diseases, and in pharmacological studies.

Some known systems for whole-body (WB) PET imaging include PET/CT (and MRI/PET) scanners that include a large number of γ-ray detectors arranged in multi-ring or multi-plane geometry to provide as much angular coverage around the field-of-view (FOV) as possible. Better angular coverage allows PET coincidence data to be collected at different angular positions across the FOV in order to achieve more complete spatial sampling and higher sensitivity. WB-PET systems are oftentimes large (e.g., filling up a room) and require subjects (or patients) be brought to the scanner. Bringing a patient to a scanner is not always the most feasible solution. For example, it can be difficult to bring a stroke patient located in a neuro-intensive-care-unit to a PET/CT scanner for verification of the patient's brain metabolic activity.

At least some known PET systems are application-specific and are optimized for a particular aspect of an application. Application-specific PET systems may include positron emission mammography systems, dedicated brain PET scanners, PET systems in the form of an imaging probe, high resolution γ-ray detectors in coincidence with low resolution X-ray detectors (Virtual-pinhole-PET, Zoom-in PET), and Plant PET systems.

WB-PET systems and application-specific PET systems are typically not designed for point-of-care applications. Examples of point-of-care applications include scenarios such as patient bed-side, treatment room, operating room, or emergency vehicle.

BRIEF DESCRIPTION OF THE DISCLOSURE

A positron emission tomography (PET) system is provided. The system includes a first detector panel including a first array of detectors, a second detector panel including a second array of detectors, said second detector panel being moveable relative to a point between the first detector panel and the second detector panel, a tracking system configured to detect a position of said second detector panel relative to the first detector panel while imaging a subject, a computing device in communication with the first detector panel, the second detector panel, and the tracking system, the computing device configured to receive coincidence data from the first and second detector panels, receive position data from the tracking system, wherein each coincidence datum of the received coincidence data is associated with a unique position datum of the received position data, and reconstruct a plurality of images based on the received coincidence data and the received position data.

A method for performing PET is provided. The method includes receiving coincidence data from a first detector panel and a second detector panel, receiving positioning data from a tracking system, and reconstructing a plurality of images. The second detector panel is movable relative to a point between the first detector panel and the second detector panel. The tracking system detects a position of the second detector panel relative to the first detector panel while imaging a subject. Each coincidence datum of the received coincidence data is associated with a unique position datum of the received position data. Reconstructing a plurality of images is based on the received coincidence data and the received position data.

DETAILED DESCRIPTION OF THE DISCLOSURE

Figure 1:
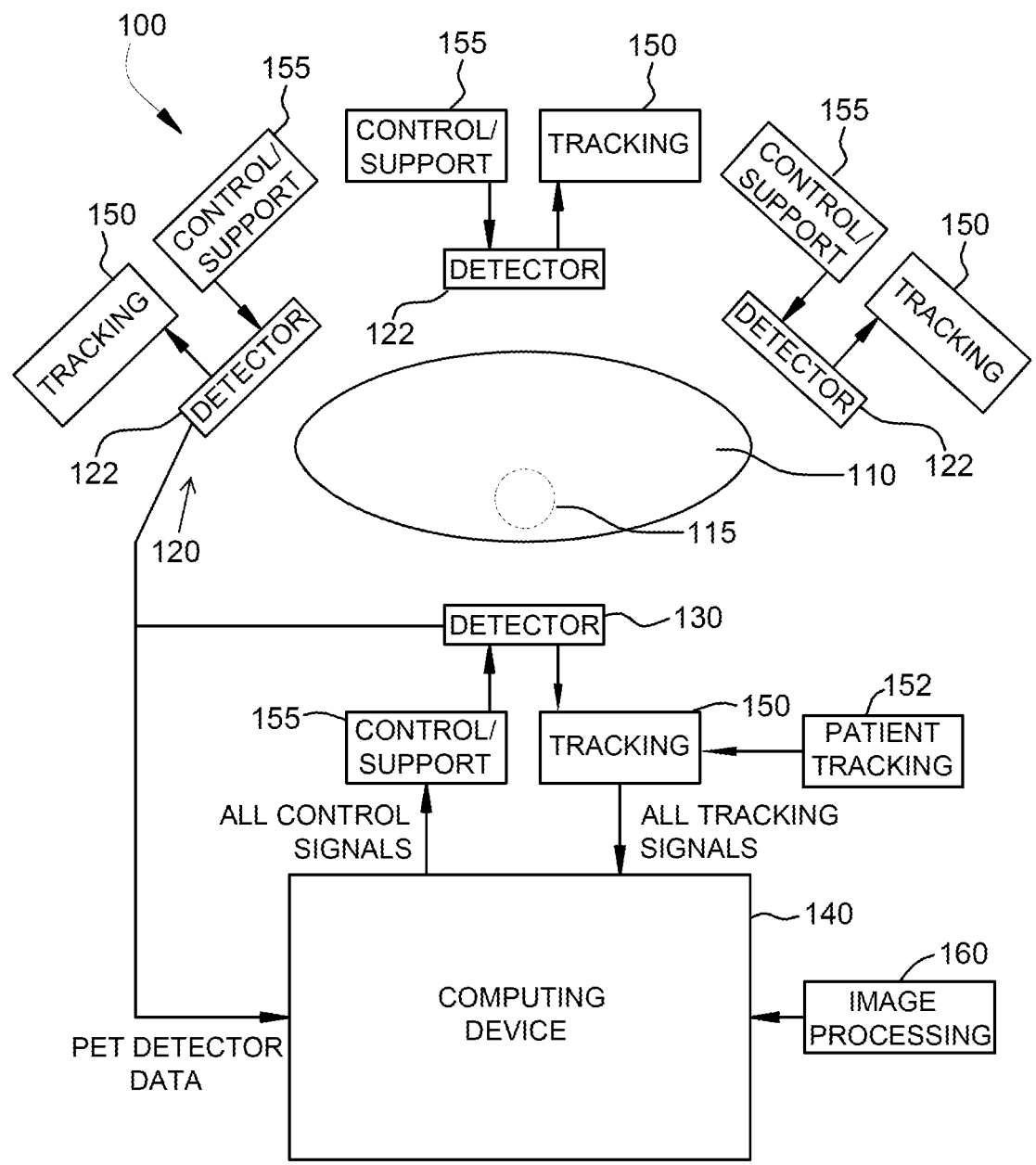
FIG. 1 is a schematic diagram illustrating an example of a PoC-PET system for imaging a target.

Systems and methods are provided herein for providing positron emission tomography (PET) of a subject for point-of-care (PoC) applications.

The exemplary PoC-PET system may be, for example, compact, self-contained and/or mobile, facilitating PET imaging in point-of-care applications by allowing it to be brought to a patient.

Conventional whole-body PET scanners use multi-ring or multi-plane geometry to achieve complete sampling of the imaging field of view (FOV) for tomographic image reconstruction. In PoC-PET systems, due to the limitation of device size and structure, PET coincidence data collected from a limited number of angular positions may be used for tomographic image reconstruction. This is similar to tomosynthesis in X-ray Computed Tomography.

Some detectors have a good timing resolution that can provide more accurate measurements of the arrival times of two annihilation γ-rays from the same positron annihilation event. The difference between their arrival times can be estimated with a lower error bound. This time-of-flight (TOF) information enables estimating a positron annihilation location along a coincidence line of response (LOR) joining the two detectors more accurately than in known systems. PET scanners that can measure TOF information produce images with better signal-to-noise ratio and contrast recovery. Additionally, in PoC-PET where coincidence data is collected from limited angles, TOF information can compensate for data from missing angles. For example, substantially artifact-free PET images may be obtained using about 50% of the angular samples of a full-ring PET system when the individual detectors have about 200 ps full-width-at-half-maximum (FWHM) timing resolution.

A PoC-PET system having detectors moving with respect to each other may use real-time tracking of PET detectors. In the example embodiment, the coincidence detection system and detector tracking system are synchronized such that the location and orientation of PET detectors may be known for each coincidence event within a specified time constraint.

In the example embodiment, PoC-PET system has sufficiently fast image reconstruction that enables providing substantially real-time feedback to the technician. Real-time implies that the reconstructed image presented to the technician is within a specified time constraint to actual data (e.g., less than a second, less than 100 ms, and the like).

To achieve fast data-collection and/or fast image reconstruction, a PoC-PET system might only reconstruct a region-of-interest (ROI). TOF information helps to select data for a truncated ROI. Thus, a PoC-PET system could provide 'targeted imaging' of an ROI for molecular imaging of specific organs or regions in a subject.

The feedback of reconstructed images within the specified time constraint to a technician enables interactive adjustment and optimization of imaging protocol and detector configuration parameters. Imaging protocol may include, but is not limited to, acquisition time, numbers and locations of the targeted organs or ROI, re-positioning or re-orienting the subject to be imaged, inclusion of additional shielding materials to block off background noise. Detector configuration parameters may include, but are not limited to, a number of detectors to be used, upper and lower thresholds of an energy window, a width of a coincidence timing window, an initial position and trajectory of each detector, a relative location of detectors from each other, and a relative location of each detector to the subject. Detector trajectory is described as a series of fixed points or splines together with a speed and waiting time at each point, which might be adjusted manually or through robotic arms.

At any moment in time, images are reconstructed based on the data collected until this time point, which may be presented to the technician who may subsequently adjust and optimize the imaging protocol and detector configuration parameters to collect additional coincidence data. The additional coincidence data may be combined with previously acquired data to jointly reconstruct PET images. Alternatively, the additional coincidence data may be reconstructed to form new PET images. This process may be repeated until a specific task requirement is satisfied.

The feedback of reconstructed images within the specified time constraint to the technician also enables the technician to interactively adjust the targeted organs or regions of interest in order to dynamically follow the radioactivity distribution and re-distribution if needed.

Based on the objective, a computing device might either move the PET detectors through robotic actuation or provide guidance to the technician on an optimal trajectory.

A PoC-PET system may include fewer detectors and be manufactured at reduced cost when compared to at least some known whole-body PET scanners. Reduced cost potentially enables deeper market penetration, which subsequently enables broad clinical utility.

Illustration of a PoC-PET Device

In at least some embodiments, a PoC-PET system may include a first, moveable PET detector panel and a second PET detector panel positioned behind a patient to detect annihilation γ-rays from the patient's body. During operation, a technician controls the first PET detector (e.g., by freehand or an articulated arm or a robotic arm) to collect coincidence data from detectors at multiple locations and angles around the desired ROI. The system also includes a tracking component for automatically registering the location and orientation of the first PET detector and feeding the position data into a data stream.

The PoC-PET system further includes an image processing component for reading in the coincidence events along with detector tracking information, in substantially real-time, to perform image reconstruction using a data model that includes detector response function and other physics parameters and that is computed based on the detector location and orientation. As the images are reconstructed by the image processing component, an updated version is displayed to provide substantially real-time feedback to the technician who may adjust the detector location and orientation to collect additional data to enhance image quality. The technician is provided visual confirmation of usable images before stopping the acquisition. In some cases, in order to finish image reconstruction in substantially real time, a simplified data model might be used at the cost of reduced image quality or quantitative accuracy. In this example, the recorded data may be stored and reconstructed by a separate image processing component using more sophisticated algorithms and/or a more accurate data model to further improve image quality.

FIG. 1 is a schematic diagram including an example PoC-PET system 100 for imaging a target in a body 110. In the example embodiment, the body 110 is a patient. The target 115 may be, for example, a particular organ of the patient such as a heart or liver. The example PoC-PET system includes an imaging probe 130 (sometimes referred to herein as an array or panel of PET detectors 130) and a PET detector array 120 including a plurality of second PET detector panels 122. The body 110 is positioned between the imaging probe 130 and the second PET detector panels 122. Together, the imaging probe 130 and the second PET detector panels 122 detect annihilation γ-rays from the target 115. In the example embodiment, the imaging probe 130 is a moveable PET detector panel. In some embodiments, both are movable. In other embodiments, the imaging probe 130 is any suitable detector to enable the PoC-PET system 100 to function as described herein.

The example PoC-PET system also includes a computing device 140 coupled with, or in communication with, the imaging probe 130 and/or the PET detector array 120. Although the computing device 140 is shown in communication with one detector panel 122, it is to be understood that the computing device 140 is in communication with each detector panel 122. The computing device 140 receives PET imaging data generated using the imaging probe 130 and/or the detector array 120 and tracking data associated with the position and orientation of the imaging probe 130. The computing device 140 provides a three-dimensional view of the target 115 based on the received imaging data and tracking data.

The example system 100 further includes a tracking system 150 for automatically registering the location and orientation of the imaging probe 130 and transmitting the imaging data into a list-mode data stream. As shown in FIG. 1, the tracking system 150 is coupled to (or in communication with) the imaging probe 130 and the detector array 120. In other embodiments, the tracking system is a component of the computing device 140. In the example system 100, the tracking system 150 is embodied by an articulated arm, where the imaging probe 130 is coupled to the arm and its position is known by the position of the arm. In some embodiments, the tracking system 150 is embodied by an optical sensor (e.g., a camera) that optically determines the position of the imaging probe 130. In yet other embodiments, the tracking system 150 may be used in controlling the position of the imaging probe 130, e.g., by providing executable instructions to the computing device 140. During operation, a technician controls the imaging probe 130 (e.g., by freehand, an articulated arm, or a robotic arm) to collect imaging data from multiple locations and angles around the target 115. In some embodiments, the motion of the imaging probe 130 is controlled either automatically or semi-automatically using the computing device 140.

In some embodiments, the system 100 further includes a patient tracking system 152 configured to track patient motion relative to the detector array 120 and the imaging probe 130 to generate patient motion information. The patient motion information may be used by the computing device 140 to limit blurring and motion artifacts in reconstructed images.

The system 100 further includes a control or support system 155. The control system 155 is configured to receive operating or system parameters from the computing device 140 and adjust the detector array 120 and/or the imaging probe 130 based on the received system parameters. Although not shown in FIG. 1 for clarity, each portion of the tracking system 150 and the control system 155 coupled to the detector panels 122 is in communication with computing device 140.

The example system 100 further includes an image processing system 160 for receiving coincidence events along with the probe tracking information in substantially real-time to perform list-mode image reconstruction using a data model that is computed by the computing device 140 based on the probe 130 location. In this example, the image processing system 160 is electrically connected to the computing device 140. As another example, the image processing system 160 may be included in the computing device 140, or connected to the computing device 140 through a network. As the images are reconstructed by the image processing system 160, an updated version is displayed on a screen (not shown) to provide substantially real-time feedback to the technician who may adjust the probe location and orientation to collect additional data to enhance image quality. The technician is provided visual confirmation of usable images on the screen before halting the acquisition. In some embodiments, the recorded data is stored to be reconstructed using more sophisticated algorithms and/or a more accurate system matrix to further improve image quality. In other embodiments, the recorded data is transmitted to a separate computing device for processing.

In at least some embodiments, the system 100 may further include a transducer and a sensor (not shown). In this example, the locations and orientations of the transducer and the sensor may also be tracked by the tracking system 150. The transducer is configured to produce signals that interact with body 110. The signals are captured by the sensor and reconstructed into images of the body 110. For example, the transducer may be an x-ray generator, a high-intensity focused ultrasound transducer, a laser source, and the like. Also, for example, the sensor may be an x-ray detector, an ultrasound detector, a light sensor, and the like. According to various aspects, the transducer and sensor may produce data that can be reconstructed by the computing device 140 to create a second modality of images. For example, the second modality of images may be co-registered with PET images acquired by imaging probe 130 using the location and orientation information of the additional transducer and sensor measured by the tracking system 150. In at least some embodiments, the detector panels 122 and the imaging probe 130 may include the transducer and/or the sensor. Alternatively, the transducer and/or the sensor may be separate from the system 100.

Figure 2:
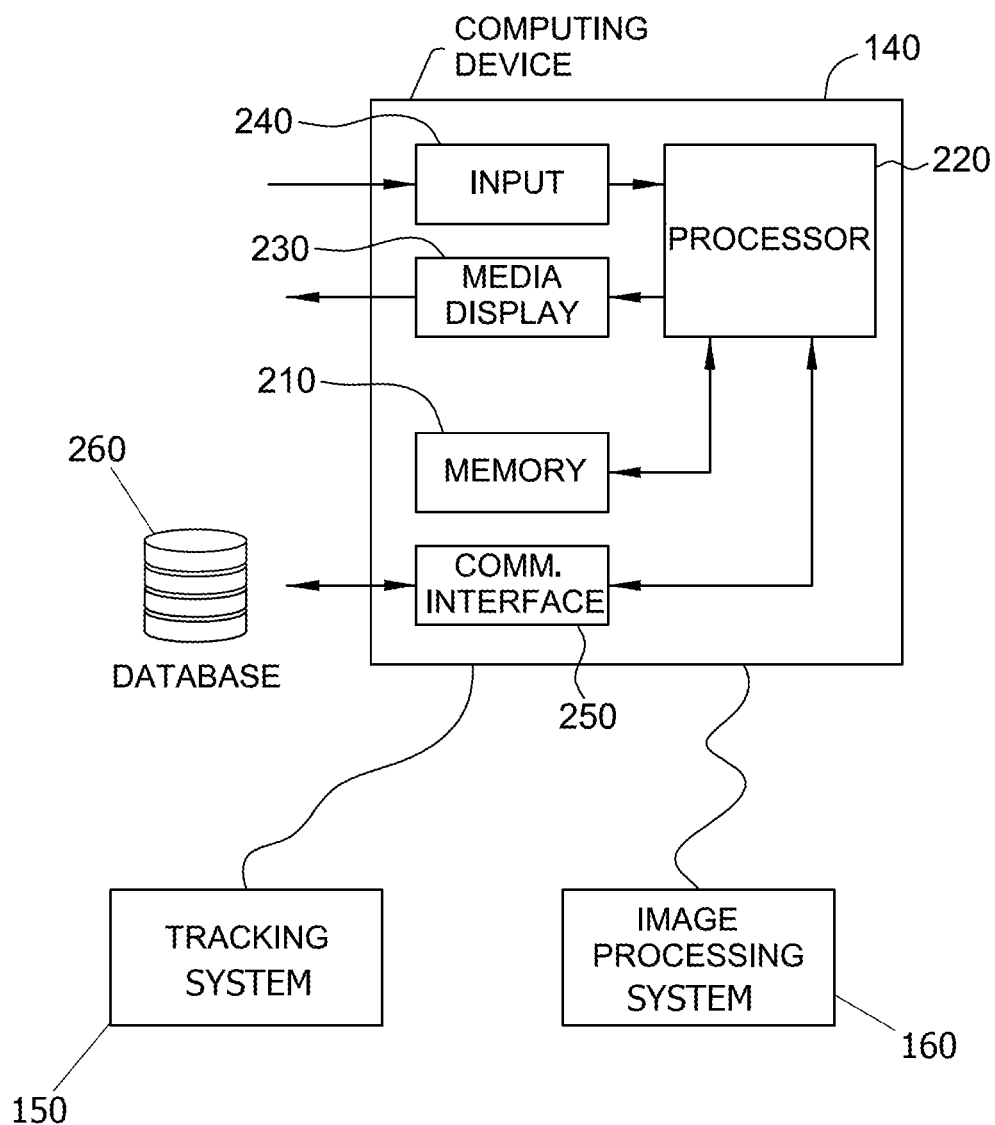
FIG. 2 is a diagram illustrating a computing device that may be included in the PoC-PET system of FIG. 1.

FIG. 2 depicts the computing device 140 for use in the example PoC-PET system 100 shown in FIG. 1. The computing device 140 includes at least one memory device 210 and a processor 220 coupled to the memory device 210. In the example embodiment, the memory device 210 may store executable instructions that, when executed by the processor 220, enable the computing device 140 to perform one or more operations described herein. In some embodiments, the processor 220 may be programmed by encoding an operation as one or more executable instructions and providing the executable instructions in the memory device.

The processor 220 may include one or more processing units (e.g., in a multi-core configuration). Further, the processor 220 may be implemented using one or more heterogeneous processor systems in which a main processor is present with secondary processors on a single chip. As another example, the processor 220 may be a symmetric multi-processor system containing multiple processors of the same type. Further, the processor 220 may be implemented using any suitable programmable circuit including one or more systems and microcontrollers, microprocessors, programmable logic controllers (PLCs), reduced instruction set circuits (RISCs), application specific integrated circuits (ASICs), programmable logic circuits, field programmable gate arrays (FPGAs), and any other circuit capable of executing the functions described herein. Further, the processor 220 may include an internal clock to monitor the timing of certain events, such as an imaging period and/or an imaging frequency. In the example embodiment, the processor 220 receives imaging data and processes the imaging data for PoC-PET.

The memory device 210 may include one or more devices that enable information such as executable instructions and/or other data to be stored and retrieved. The memory device 210 may include one or more computer readable media, such as, dynamic random access memory (DRAM), static random access memory (SRAM), a solid state disk, and/or a hard disk. The memory device 210 may be configured to store application source code, application object code, source code portions of interest, object code portions of interest, configuration data, execution events and/or any other type of data.

The computing device 140 may also include a media display 230 and an input interface 240. The media display 230 is coupled with the processor 220, and presents information, such as user-configurable settings or PoC-PET images, to a user, such as a technician, doctor, or other user. The media display 230 may include any suitable media display that enables the computing device to function as described herein, such as, e.g., a cathode ray tube (CRT), a liquid crystal display (LCD), an organic light emitting diode (OLED) display, an LED matrix display, and an "electronic ink" display. Further, the media display 230 may include more than one media display.

The input interface 240 is coupled with the processor 220 and is configured to receive input from the user (e.g., the technician). The input interface 240 may include a plurality of push buttons that allow a user to cycle through user-configurable settings and/or user-selectable options corresponding to the settings. Alternatively, the input interface 240 may include any suitable input device that enables the computing device 140 to function as described herein, such as, e.g., a keyboard, a pointing device, a mouse, a stylus, a touch sensitive panel (e.g., a touch pad or a touch screen), a gyroscope, an accelerometer, a position detector, and/or an audio interface. Additionally, a single component, such as a touch screen, may function as both the media display 230 and the input interface 240.

The computing device 140 may further include a communications interface 250. The communications interface 250 is coupled with the processor 220, and enables the processor 220 (or the computing device 140) to communicate with one or more components of the PoC-PET system, other computing devices, and/or components external to the PoC-PET system. For example, the communications interface 250 may be in communication with an external database 260 that stores previously acquired data and system parameters. In another example, the communications interface 250 facilitates communication between the computing device 140 with the tracking system 150 and the image processing system 160.

Figure 3:
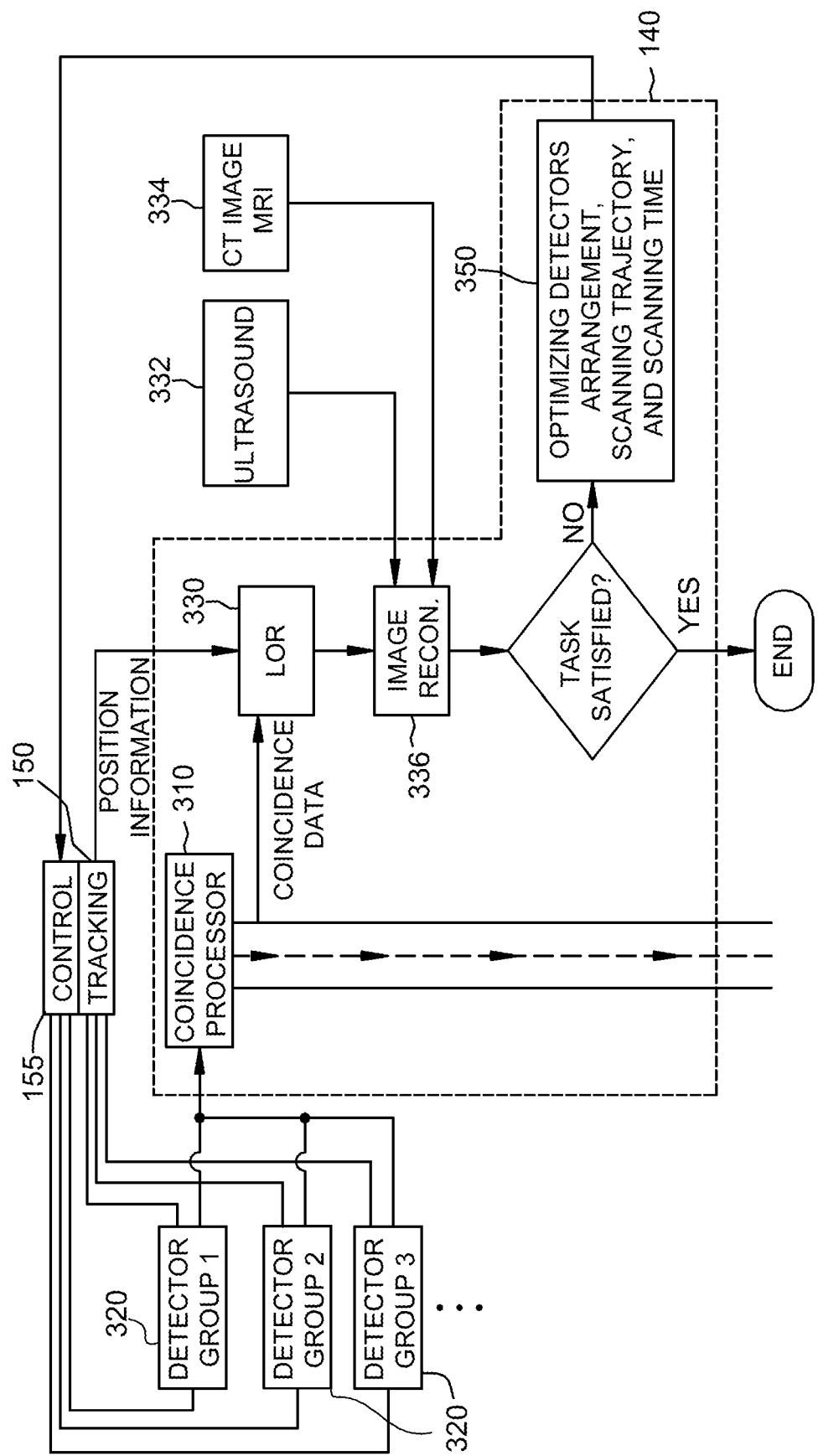
FIG. 3 is a flow diagram including components for the detector, the control and tracking, the data processing and the image precession representing a process that may be performed by the PoC-PET system shown in FIG. 1.

FIG. 3 is a hybrid flow diagram 300 including components for the detector, the computing device 140, the tracking system 150, and the control system 155 (each shown in FIG. 1) representing a process that may be performed by the PoC-PET system 100 shown in FIG. 1. The computing device 140 includes at least one data acquisition channel for each detector group 320 and a coincidence processor 310 coupled to each of the acquisition channels. Each detector group 320 includes one or more detector similar to the detector panels 122 (shown in FIG. 1). In some embodiments, the coincidence processor 310 and the processor of the computing device 140 may be implemented as the same processor. In some embodiments, the coincidence processor 310 and the processor of the computing device 140 may be two separate processors each may be programmed by encoding an operation as one or more executable instructions and providing the executable instructions in the memory device.

In the example embodiment, the computing device 140 combines position information associated with the detector groups 320 from the tracking system 150 with coincidence data from the coincidence processor 310 to generate coincidence LOR data 330. The computing device 140 may be configured to receive image data such as an ultrasound 332 or a CT or MRI image 334. The computing device 140 combines the LOR data 330 with the optional image data 332 or 334 to carry out the image reconstruction function 336. If the images have a sufficient quality to satisfy the task such as patient diagnosis, the imaging procedure can be halted by the operator. If the image does not have a sufficient quality for the task, the computing device 140 optimizes 350 the arrangement of detector groups 320 and other system parameters to reconstruct images with sufficient image quality for the desired task. The computing device 140 then transmits the optimized system parameters to the control system 155 (shown in FIG. 1) to adjust the detector groups 320.

Prototype PoC-PET Device

To determine the feasibility of PoC-PET systems, a prototype was developed. FIGS. 4 to 7 include diagrams illustrating an example PoC-PET system such as, e.g., the example PoC-PET system 100 shown in FIG. 1.

Figure 4:
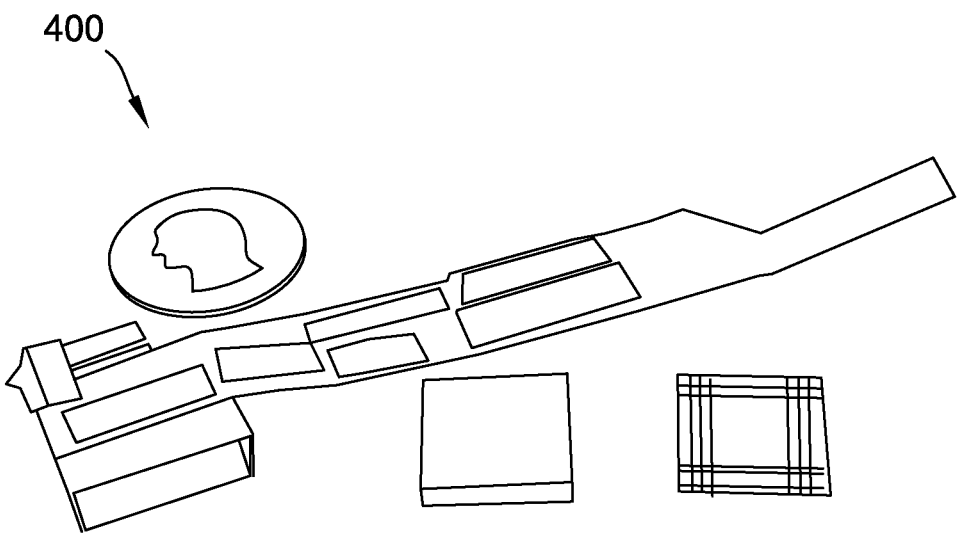
FIGS. 4 to 7 are examples of components of a PoC-PET system.

FIG. 4 includes a compact PET block detector 400 for use in the example system. In one embodiment, the compact PET block detector 400 may include a LYSO array (20×20 crystals, 0.74×0.74×3 mm each) and a silicon photomultiplier (SiPM) array (4×4). The timing resolution of the prototype detector may be about 600 ps Full Width at Half Maximum (FWHM) due to the multiplexing of SiPM signals using a charge-division resistive network. The detector 400 may be self-contained (including pre-amplifier boards and a power supply board) and is suitable for determining the feasibility of PoC-PET.

Figure 5:
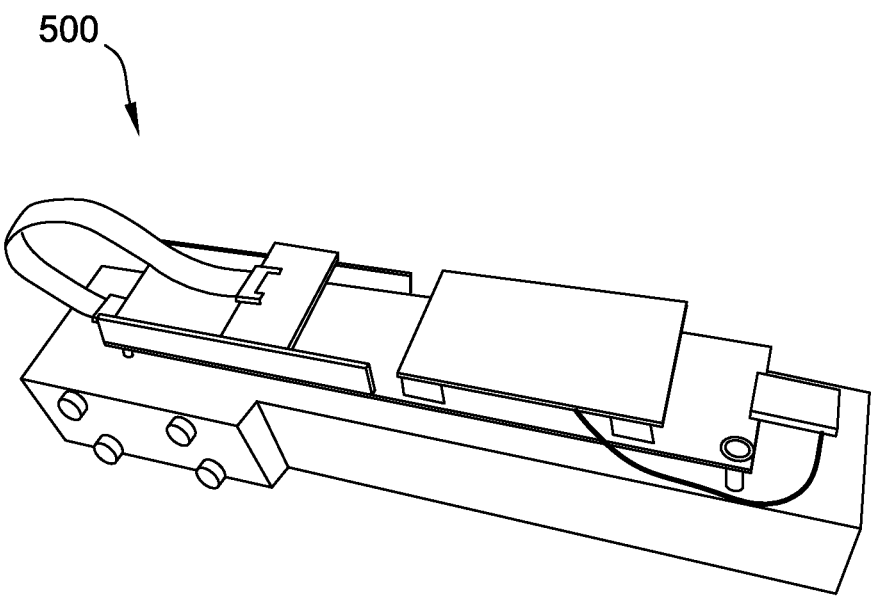

FIG. 5 includes a prototype imaging probe 500 usable as probe 130 (shown in FIG. 1) containing a detector module such as the detector 400 shown in FIG. 4. The detector module may be mounted in a plastic housing to form a prototype hand-held imaging probe.

Figure 6:
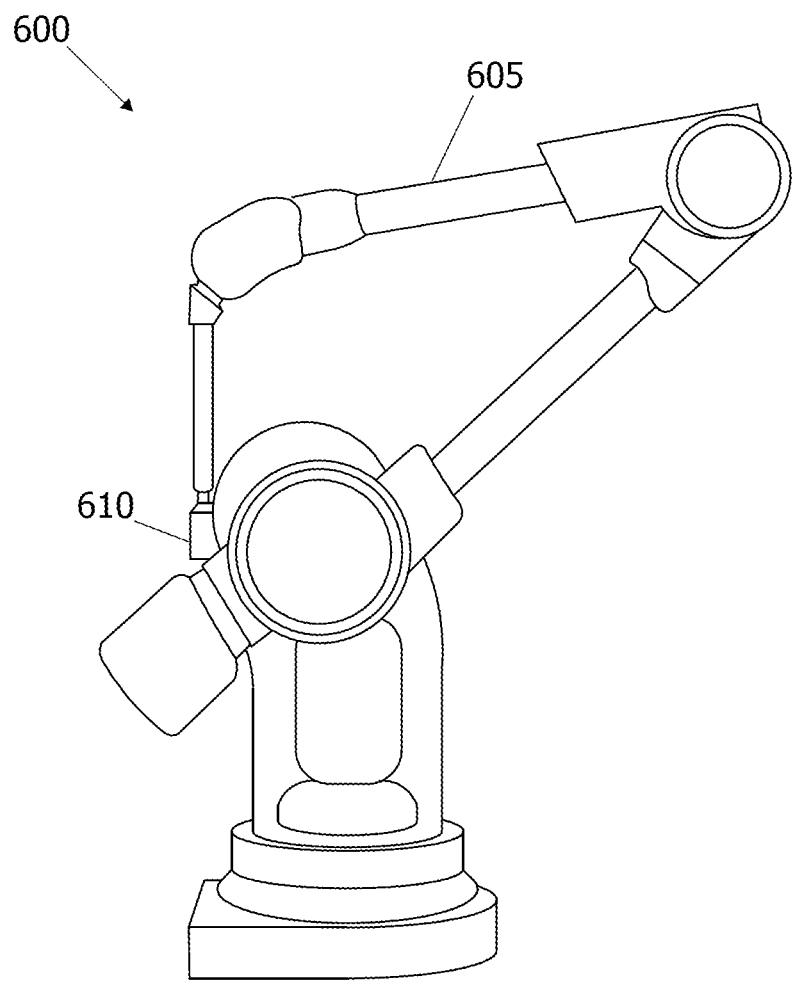

FIG. 6 includes an example of a tracking system 600 for tracking the location and orientation of the imaging probe such as the imaging probe 500 shown in FIG. 5. Many tracking technologies have been adapted in medical applications such as imaging and therapeutic interventions. For example, the tracking system 600 may include a MicroScribe 3D Digitizer MX system for tracking the location and orientation of the imaging probe. The example tracking system 600 may be a mechanical tracking device that can digitize the 3D space of about 0.63 m in radius with a spatial resolution of about 0.05 mm. During operation, the tracking system may continuously refresh and record the coordinates and the Euler rotation angles of the stylus at about 50 frames per second. The tracking system 600 includes an actuatable arm 605 configured to move by the operator.

The compact imaging probe 500 may be attached to a stylus holder 610 of the tracking system. The reported coordinates and angles from the tracking system 600 may be used to calculate the location and normal vectors of the maneuverable PET imaging probe 500. The calculated probe location may be incorporated into the PET list-mode data stream using time stamps created by the PET data acquisition system and the tracking system.

Figure 7:
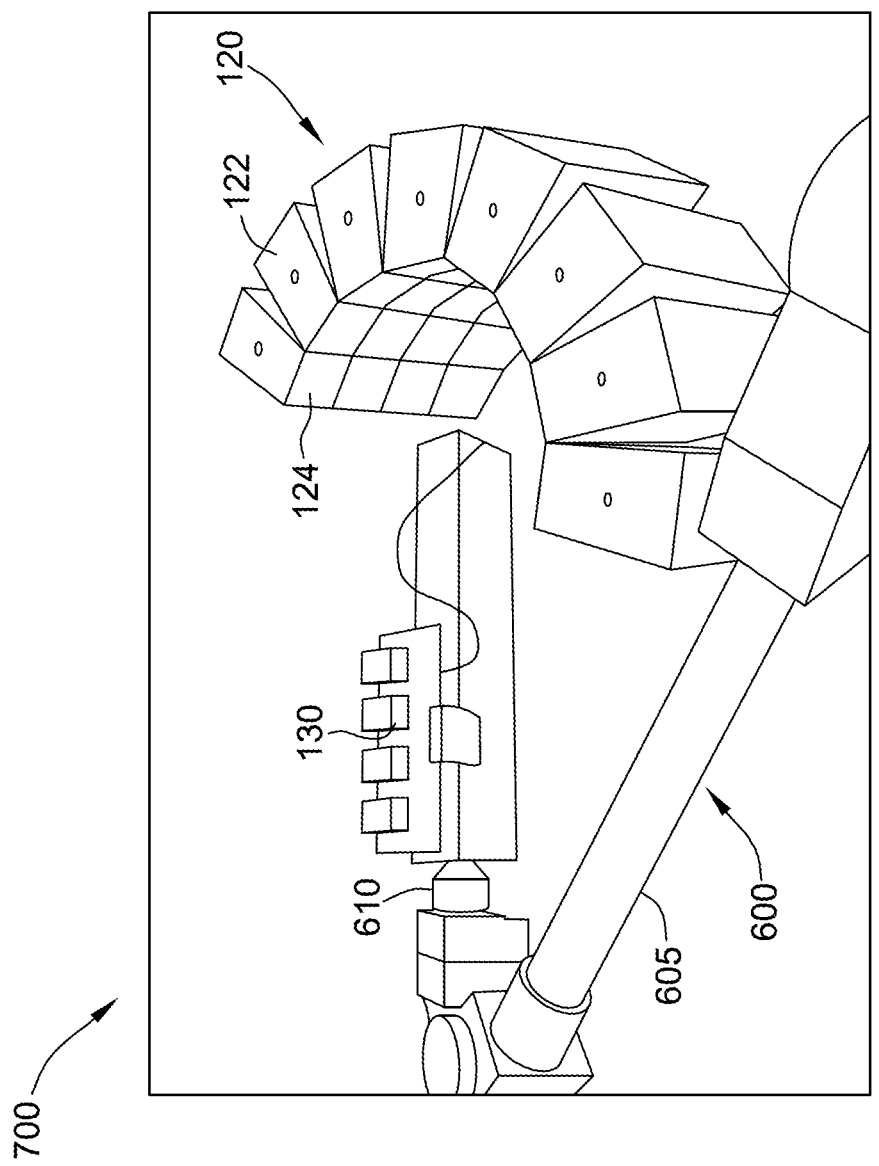

FIG. 7 includes a diagram 700 showing an example of a setup including the imaging probe 130 (shown in FIG. 1)

with a plurality of PET detectors 124. In the example embodiment, the imaging probe 130 is probe 500 and is coupled to the stylus holder 610 of the tracking system 600 shown in FIG. 6. The imaging probe 130 may be set up to be in coincidence with the PET detectors 124, for example, 32 detectors arranged to form a half-ring geometry. In the illustrated embodiment, eight detector panels 122 of four detectors 124 are shown. Alternatively, the system may include a different number of detectors 124 or detector panels 122. In at least some embodiments, the half-ring geometry may include a radius of about 87 mm. Each detector 124 may include 20×20 LSO crystals, and each crystal may be of 1.6×1.6×10 mm. Detector signals are transmitted to a computing device such as the computing device 140 shown in FIG. 1. In the prototype system, the computing device may include a set of QuickSilver electronics that may be used in PET scanners. In this example, coincidence events between the imaging probe 130 and the other 32 block detectors 124 may be extracted from the list-mode data using a sorting code.

Before the list-mode data may be reconstructed, the coordinate system of the tracking system 600 may be co-registered to the coordinate system of the PET detectors 124. For example, the coordinate systems may be co-registered by selecting four (or more) known locations in the half-ring PET coordinate system and inputting their coordinates in a matrix, P, measuring the coordinates of the four (or more) locations using a stylus of the tracking system 600 to obtain a matrix, L, and estimating the transformation matrix, T, by solving P=T*L using a least-squares estimation procedure. The exemplary calibration may be performed once, for example, if the base of the tracking system is fixed relative to the plurality of PET detectors.

For performing image reconstruction, the prototype PoC-PET system may include, for example, a list-mode, graphic processing unit-based TOF image reconstruction framework with the capability to handle dynamically changing system geometry. The moving probe trajectory may be modeled as a series of fixed locations and orientations, with time duration at each location limited by the refresh rate of the tracking system (e.g., about 20 ms). In contrast to conventional image reconstruction, extra information from the tracking system 600 may be integrated to calculate the dynamic system geometry on-the-fly. For example, the location information may be encoded as $p_d$ for positioning and $r_d$ for time duration, where, d=1, . . . , n (number of locations). In the current implementation of the algorithm, the expectation maximization (EM) algorithm may be used to seek the maximum likelihood (ML) solution for radionuclide distribution. In at least some other embodiments, alternative algorithms may be used for image reconstruction to provide the substantially real-time feedback to an operator.

In the prototype system, time-of-flight information may be incorporated as an independent Gaussian kernel applied along the direction of the LOR of each event. The center of the Gaussian kernel (TOF center) is determined by the time difference between two annihilation γ-rays from the same positron annihilation event while its FWHM is determined by the coincidence timing resolution of the PET detectors 130 and 122 (shown in FIG. 1). If the individual detector has a 200 ps FWHM timing resolution, the coincidence timing resolution of the system may be 282 ps FWHM. The corresponding Gaussian kernel used for reconstruction may have a FWHM of 42.3 mm. In forward and backward operator, the weights (system matrix) along a LOR may be multiplied by this Gaussian kernel, thus voxels far away from the TOF center may receive lower weights in comparison to voxels near the TOF center. In at least some other embodiments, the TOF information may be incorporated into image reconstruction using alternative algorithms and/or smoothing kernels.

In the prototype system, an image reconstruction method may be implemented on a graphics processing unit (GPU) card. In one embodiment, the GPU is an Nvidia GTX Titan GPU. Alternatively, the image reconstruction method may be implemented by a different GPU or graphics processing system. The reconstruction time may be proportional to the number of list-mode events. In one embodiment, a reconstruction speed of about 0.83 million events per second per iteration may be observed for an image in a 256×256×160 voxel rectilinear space with each voxel being a 0.8 mm cube.

Figure 8:
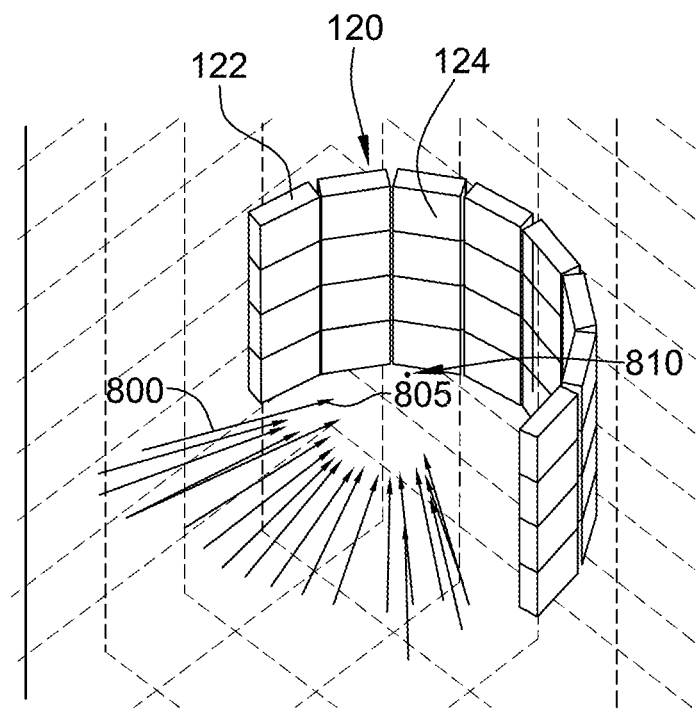
FIG. 8 is an example configuration for the experimental setup shown in FIG. 6.
Figure 8:
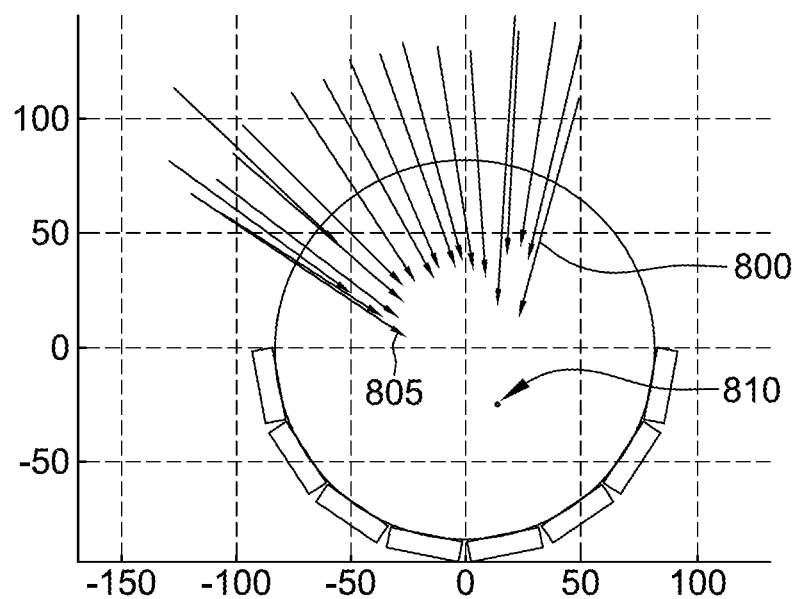

In further determining the feasibility of PoC-PET, an experiment was conducted using the prototype system shown in FIGS. 4 to 7. FIG. 8 includes a perspective view and a top plan view of an example configuration for the experimental setup shown in FIG. 7. As shown in FIG. 8, arrows 800 denote an orientation of the imaging probe 130 (not shown in FIG. 7). Each arrow 800 includes an arrow tip 805. The arrow tip 805 is the location of the center of the detector block in the imaging probe 130. The dot in the Field Of View (FOV) is the location of a Na-22 point source or target 810.

The Na-22 point source 810 (about 4 µCi) was placed at a location slightly off center of the half-ring geometry of the plurality of PET detectors. The imaging probe was placed at 20 random locations with the imaging probe 130 roughly facing the point source. The tip 805 and direction of the 20 arrows 800 represent the center and the normal vector of the detector array in the imaging probe 130 at the corresponding locations, respectively. The angular sampling covered by the probe is roughly 80 degrees. Since the LYSO crystals in the prototype imaging probe are 3 mm thick, the detection efficiency may be low. In this example, a total of approximately 300,000 coincidence events were collected in 25 min (75 sec/angle).

Figure 9:
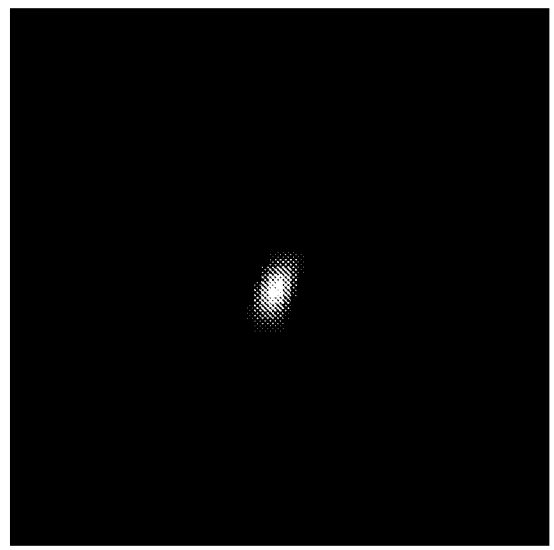
FIGS. 9 and 10 are examples of reconstructed images.
Figure 10:
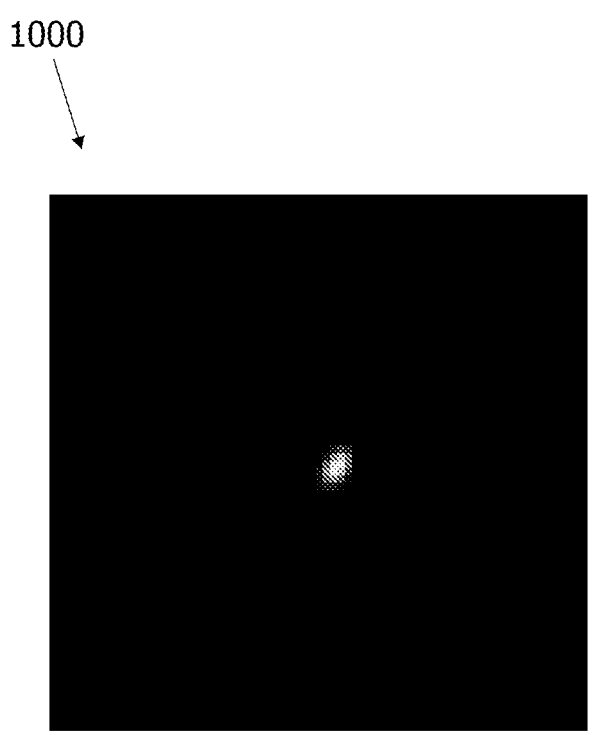

FIG. 9 shows an example of a reconstructed image 900 of a point source (e.g., point source 810, shown in FIG. 8) after the 8th iteration within the example experiment, which in this example took the GPU approximately 2-3 seconds to finish. This result is consistent with a Monte Carlo (MC) simulation using GATE, a MC simulation toolkit widely used to study PET and SPECT systems. The imaging probe (at 20 locations) and 32 PET detectors were modeled in GATE using the same geometry shown in FIG. 7. FIG. 10 illustrates example of a reconstructed image 1000 of the point source within the MC simulation. The experimental image 900 and the MC image 1000 show the same characteristics except that the former has slightly lower resolution, which may be due to tracking and registration inaccuracy in the experiment.

The preceding experiment demonstrates the ability to use in-kind PET detectors, electronics, and tracking equipment to establish a platform for PoC-PET systems. Other experiments involving these PoC-PET systems may be conducted to establish and calibrate the synchronization between the coincidence detection system (QuickSilver electronics) and the tracking system (MicroScribe) to enable collection of data by maneuvering the imaging probe freehand, as opposed to 20 stationary locations.

Monte Carlo Simulation of a PoC-PET System

In further determining the feasibility of PoC-PET, a Monte Carlo (MC) simulation experiment was conducted to evaluate the performance and limitations of PoC-PET. FIGS. 11 to 14 relate to the simulation of a prototype PoC-PET system using GATE.

Figure 11:
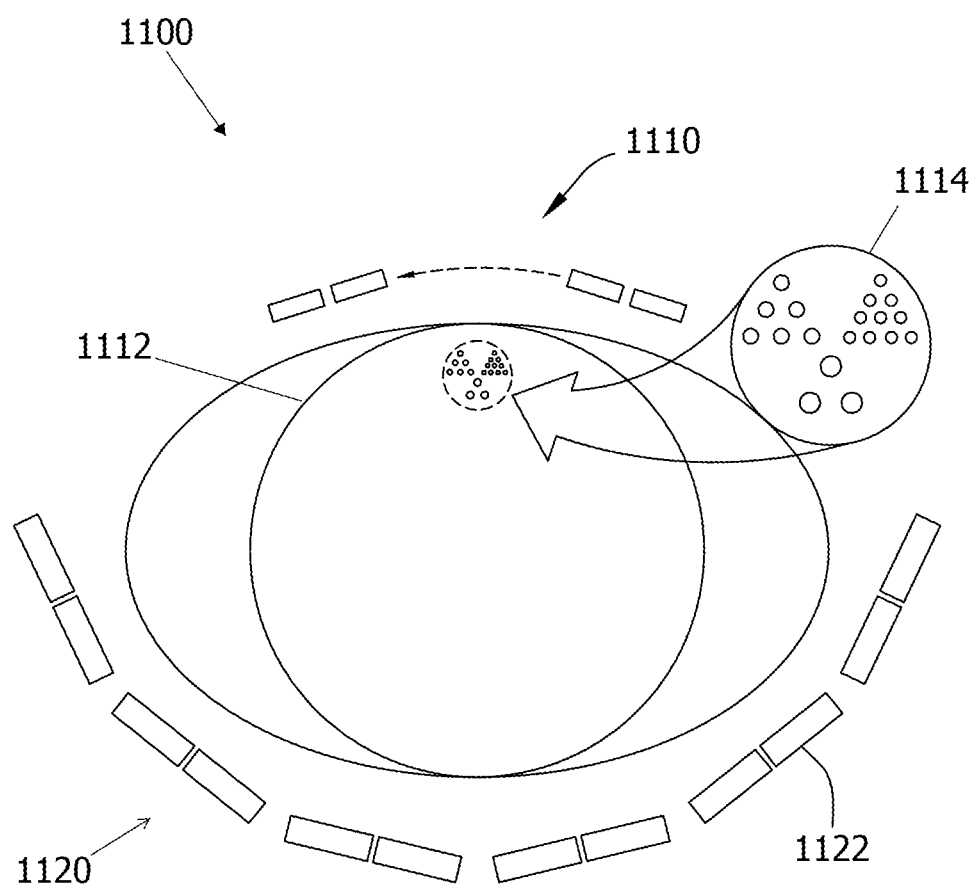
FIG. 11 is a diagram illustrating an example setup for a Monte Carlo simulation of a PoC-PET system.

FIG. 11 includes a MC simulation 1110 of a PoC-PET system using GATE. The MC simulation 1110 was configured to simulate data acquired of a body 1112 that includes a test object 1114. The body 1112 imaged to mimic a patient torso in the MC simulation 1110 was an elliptical tube with the following parameters: (1) semi-major axis: 20 cm; (2) semi-minor axis: 13 cm; (3) tube height: 20 cm; (4) material: water. Radioactivity in the body 1112 included a uniform background within the central cylindrical volume (radius=13 cm, height=20 cm). The test object 1114 included 3 sectors of rods or holes to simulate lesions (radius=1, 1.5 and 2.0 mm, respectively; height=30 mm). The spacing between the rods was two times the diameter of the rods (typical Derenzo phantom pattern). The radionuclide used was F-18; activity concentration was 0.14 µCi/mL in the background (equivalent to 9.8 mCi of activity uniformly distributed in a 70 kg person).

As shown in FIG. 11, a front panel 1110 representing the imaging probe 130 (shown in FIG. 1) was placed at 20 locations around body 1112 to collect coincidence events. In the example MC simulation 1100, the front panel 1110 included 8 PET block detectors (2× transaxially, 4× axially). Each detector includes 16×16 LSO crystals of 1.92×1.92×10 mm each, arranged in 2 mm pitch. The acquisition time was 1 min/location. The lesion/background contrast ratio ranged from 6:1 to 11:1 to simulate background noise during acquisition. The front panel 1110 was moved from one side of the lesions to the other side in 20 steps to collect coincidence events for a total of 20 minutes (1 min/step). An array 1120 of detector panels 1122 was positioned around the body 1112 in coincidence with the front panel 1110. In the example MC simulation 1100, the detector array 1120 included 24 PET block detectors arranged to form 6 detector panels 1122 of 2×2 arrays. Each PET block detector of the detector panels 1122 includes 16×16 LSO crystals of 2.92× 2.92×15 mm each, arranged in 3 mm pitch. Additional system parameters include: (1) energy resolution: 15% FWHM; (2) energy window: 350-650 keV; (3) timing resolution: 200 (or 500) ps FWHM for individual detectors, 282 (or 705) ps FWHM for coincidence timing.

Figure 12:
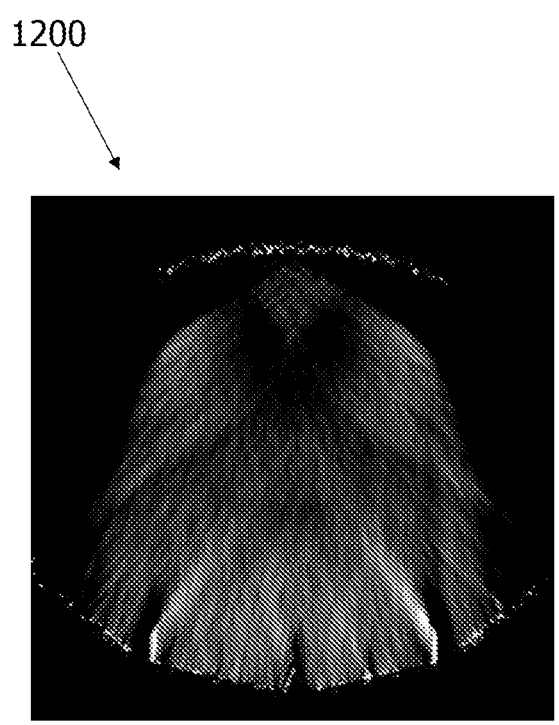
FIG. 12 is an example of a reconstructed image using non-TOF.
Figure 13:
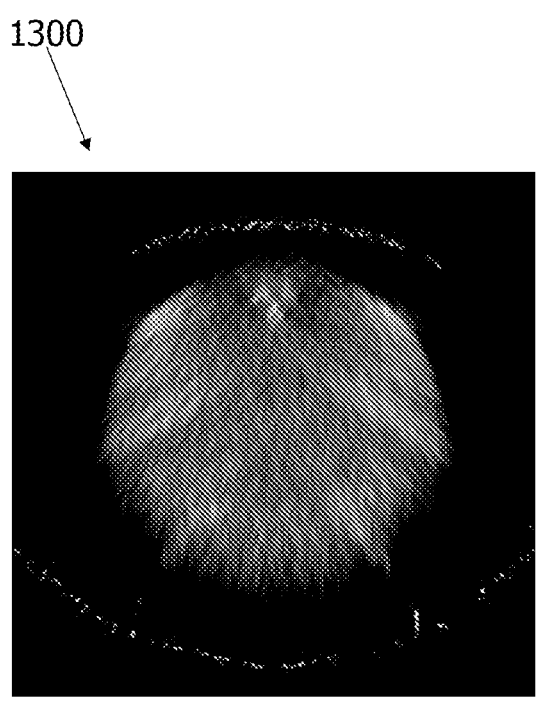
FIG. 13 is an example of an image from TOF detectors with 500 ps timing resolution.
Figure 14:
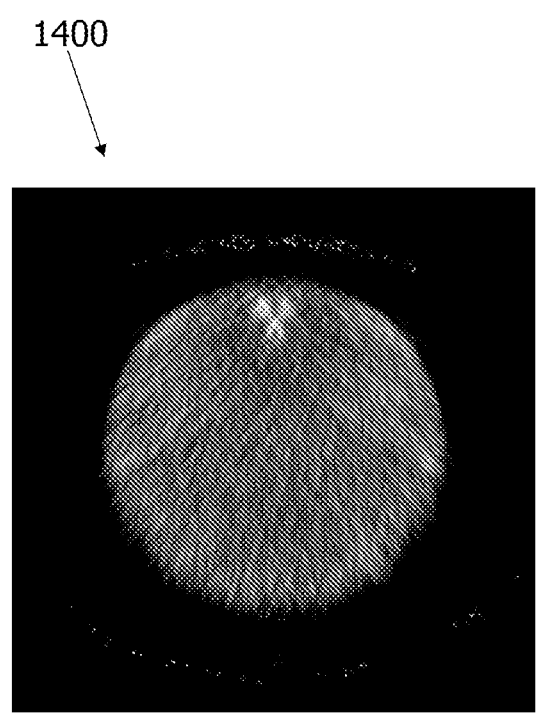
FIG. 14 is an example of an image from TOF detectors with 200 ps timing resolution.

In the examples herein, FIG. 12 includes a reconstructed image 1200 without using TOF information to estimate LOR data. FIG. 13 includes an image 1300 from TOF detectors with 500 ps timing resolution. FIG. 14 includes an image 1400 from TOF detectors with 200 ps timing resolution. As shown in FIGS. 13 and 14, increasing the timing resolution may provide additional information from the images. However, even with detectors of 500 ps FWHM timing resolution (which is easily achievable by current PET technology standards), one can begin to resolve the 4 mm diameter hot lesions in the ROI.

Figure 15:
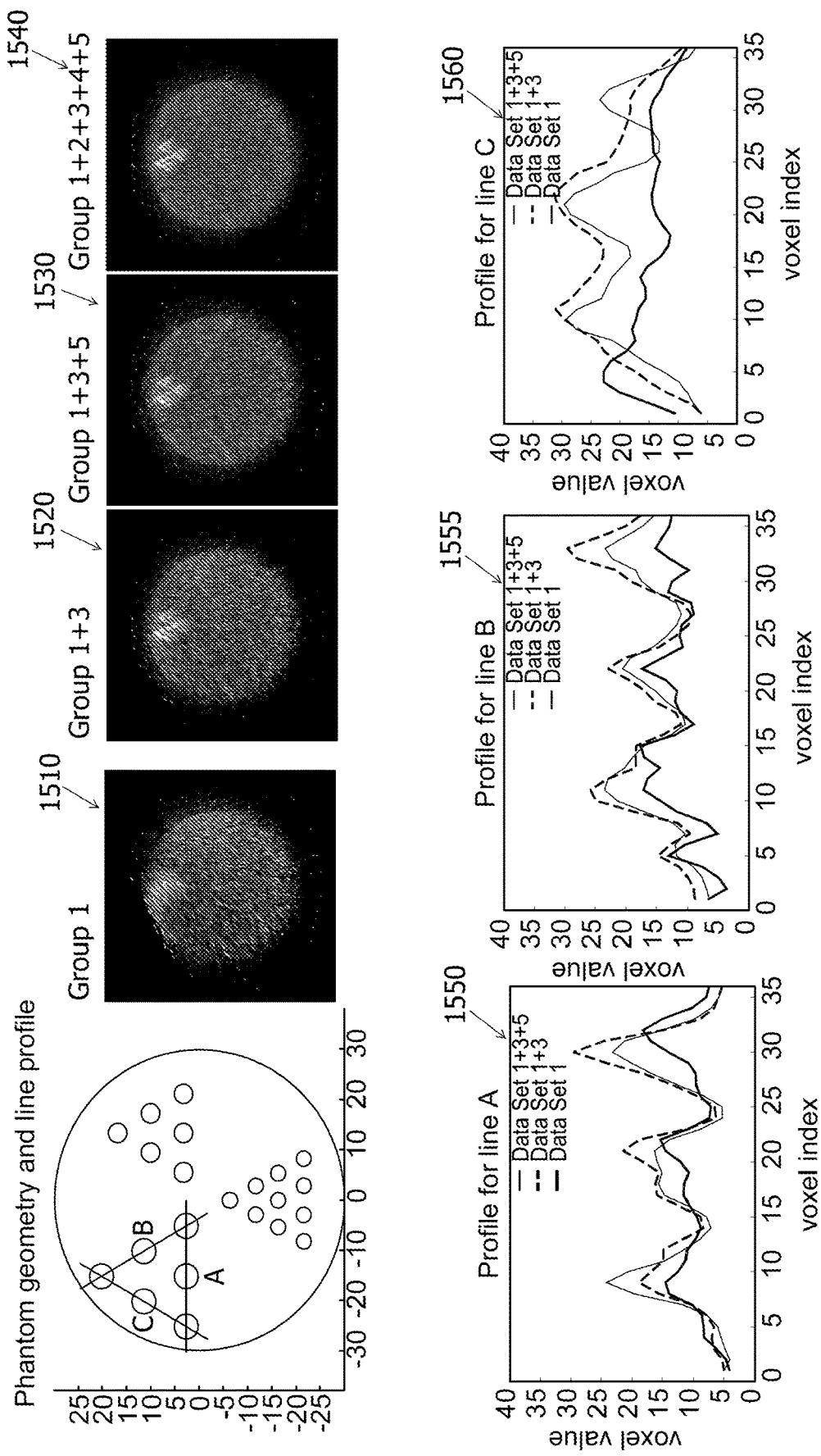
FIG. 15 is a diagram illustrating an example of the similar condition as FIG. 14 except that the images were reconstructed using one-fifth, two-fifth, three-fifth, or all of the coincidence data to illustrate how a PoC-PET system may provide real-time feedback to a technician as data is acquired.

In another example experiment, the PoC-PET system shown in FIGS. 1 and 11 were compared to another embodiment. In the experiment, a test object within a body similar to the body 1112 and the test object 1114 shown in FIG. 11 was imaged. The test object included three sectors of rods or holes with a rod radius of 3 mm for a first sector, 4 mm for a second sector, and 5 mm for a third sector. FIG. 15 illustrates data collected from the PoC-PET system shown in FIGS. 1 and 11 with the same system parameters as FIG. 14 (200 ps timing resolution), except that the images were reconstructed using one-fifth, two-fifths, three-fifths, or all of the coincidence data to illustrate how a PoC-PET system may provide real-time feedback to a technician as data is acquired. In the illustrated embodiment, the images were reconstructed using four, eight, twelve, and twenty probe locations (with twenty representing the total number of probe locations). Each "Group" as shown in FIG. 15 refers to one-fifth of the total number of probe locations.

To evaluate the value of the real-time feedback and interactive adjustment capability of the PoC-PET system, data from the Monte Carlo simulation study was reconstructed in four different ways. A first group of data was collected and reconstructed from one-fifth of the total number of imaging probe locations. As shown in FIG. 15, an image 1510 with Group 1 of the imaging probe locations represents what an operator may see on the screen when a scan is first started. Given the relatively poor image quality, the operator may choose to increase the scan time and move the imaging probe around the patient to increase the angular sampling. A second group of list-mode data was acquired from new probe locations in the reconstruction. An updated image 1520 of Groups 1 and 3 represents what an operator may see on the screen after he or she changes the imaging probe location and acquires more data. As the scan progresses, the image quality may improve. In the example experiment, yet another group of list-mode data was acquired from additional new probe locations in the reconstruction. Another updated image 1530 of Groups 1, 3, and 5 shows further improvement when compared to the first two images. Additionally, in the illustrated embodiment, three graphs 1550, 1555, 1560 depict voxel values for the images 1510, 1520, 1530 along three lines A, B, C of a test object (e.g., similar to the test object 1114, shown in FIG. 11). In the example embodiment, each line includes a plurality of holes or rods to simulate lesions.

The operator may halt the imaging session if the image quality is considered usable. Alternatively, the operator may choose to continue the scan and dynamically adjust the imaging probe to acquire more data from more locations. In the example experiment, the results may be represented by an image 1640 which includes coincidence events from all five Groups of imaging probe locations.

Figure 16:
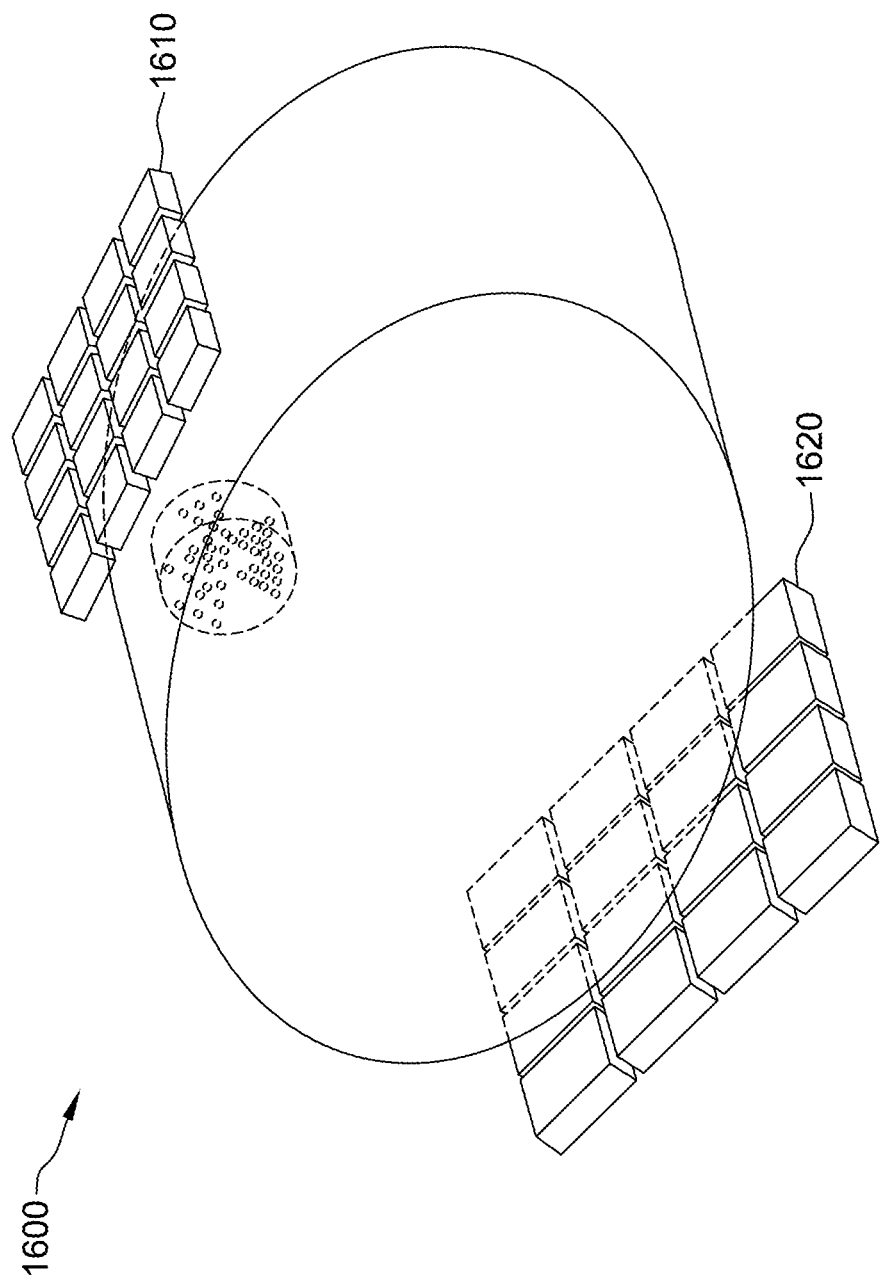
FIG. 16 is a diagram illustrating an example of an illustration of another embodiment of a PoC-PET system using fewer detectors.

The example PoC-PET system illustrated in FIGS. 1 and 11 employ a moveable front detector (imaging probe) and stationary second (rear) detector panels. Another potential embodiment, as illustrated in the example of FIG. 16, includes a smaller rear detector panel 1620 that moves synchronously with a front panel 1610 such that the center of both panels always face the center of the ROI. Although the front and back panels 1610, 1620 are referred to as "front" and "back", it is to be understood that "front" and "back" are not associated with the orientation of the body or test object with the system 1600. Both panels move relative to a point between the front and back panels 1610, 1620. The first embodiment (shown in FIGS. 1 and 11) may provide higher overall system sensitivity, while the second embodiment (shown in FIG. 16) may provide an opportunity to further reduce the cost of the system.

It should be appreciated that in some embodiments of the PoC-PET system, the number and dimensions of the detectors in the front and rear panels may differ. In some embodiments, the angular coverage, timing resolution of detectors and scan duration may also vary.

The example PoC-PET system described herein facilitate supporting molecular imaging at point-of-care such as, but not limited to, bed-side, treatment room, surgical operating room, an emergency vehicle or carrier, and the like.

In contrast to WB-PET (Whole Body PET) scanners typically used for clinical PET imaging, the exemplary embodiments are designed to image a user-selected ROI (Region-Of-Interest) or target. The system adopts maneuverable PET detector panels (primary detector panels) that works in conjunction with a second or multiple additional PET detector panels (secondary detector panels), which could be either static or moveable as well. The system allows an operator to control the primary detector panels (freely by hand or a robotic arm) to collect coincidence data from multiple locations and angles around the desired ROI to provide better sampling for image reconstruction and display. For example, the control of the maneuverable detector panels can be manual, semi-automatic or fully automatic with computer programs.

In at least some embodiments, when the primary detector panel or imaging probe is maneuvered to image a subject, the secondary detector panels may move in conjunction to collect the data efficiently. The movement of the secondary detector panels may be automatically controlled by a computer algorithm based on maximizing the information that the data carries to get better image quality or optimizing an imaging task.

A tracking system may automatically register the location and orientation of all detector panels and feed the information into a data stream of PET data. An image reconstruction engine of a computing device may read the coincidence events along with detector location information in real-time to perform list-mode image reconstruction using a data model that can be computed on-the-fly for a dynamically changing detector location. As the image is continuously reconstructed, an updated version may be displayed (or continuously displayed) through an image display mechanism to provide near real-time feedback to the operator who can interactively adjust the detector location and orientation to collect additional data to further enhance the image quality as needed. Computer guidance may also be adopted to inform the operator of optimal scanning trajectory in real-time.

The image display mechanism is used to interactively display the 3D medical image to the operator, enabling the operator to have more flexibility in viewing the image than a traditional displaying method. A real-time projection engine renders the current 3D image stacks to user selected types of visualization (maximum intensity projection, mean intensity projection, etc.), while the user can manipulate the 3D image (rotate, zoom in/out, slice, segment) freely using user input devices.

When sufficient sampling and counting statistics are obtained through the user-controlled trajectory and pace, the operator may have visual confirmation of usable images on the screen before halting the acquisition. In this example, the recorded data can be reconstructed offline later using more sophisticated algorithms and/or more accurate system response matrix to further improve the image quality.

According to various exemplary embodiments herein, two or more gamma ray detector panels may be mounted on a tracking device or tracked by separate tracking mechanisms. The tracking mechanism may include, but is not limited to, passive tracking using mechanical devices or cameras, active tracking with a radiofrequency wave emitter or laser source, robotic arms that provide both mechanical support and tracking functions at once, and the like.

The coincidence data from PET data acquisition system and detector location data from tracking device may be time stamped or synchronized in real time.

According to various exemplary embodiments, an on-the-fly image processor may read PET coincidence data and detector locations from the tracking device and reconstruct the 3D images in real time to provide relatively instant feedback as the scanning is in progress (simultaneous data acquisition and image reconstruction).

A real time image visualizer may render the 3D image stack into a user selected type of visualization. Users may control the visualizer interactively using a user interface device in order to enhance the interpretation of the acquired images. Current scanning trajectory and any computer guidance may also be displayed through this visualizer.

According to various exemplary embodiments herein, provided is a mechanism that enables a user to adjust the imaging protocol and detector configuration parameters to improve the overall image quality based on the real-time feedback from current images, until the requirement of the task is satisfied. This may be done by an operator, an operator with computer guidance, or fully automatic computer optimization algorithm. Also, an offline image processor may reconstruct the 3D images using a more accurate data model.

The exemplary embodiments herein provide "targeted imaging" of a ROI (Region-of-Interest) to support molecular imaging for specific organs or regions.

The real-time feedback of reconstructed image enables an operator to interactively adjust imaging protocol and detector configuration parameters to gather as much or little data as desired, until the task is satisfied. This flexibility enables the system to support a wide range of applications.

According to various exemplary embodiments, the system is compact, self-contained and mobile, enabling the system to be brought to a patient in point-of-care environments to provide molecular imaging applications such as image assisted chemotherapy that may not be supported by current PET technologies.

This system may use a reduced number of detectors and thus can be made at lower-cost when compared to a WB-PET scanner. The issue of missing data from a portion of angular positions may be partially compensated by TOF information from TOF detectors. The maneuverable detectors provide the flexibility to scan the desired ROI from angles and locations of the operator's choice.

According to various exemplary embodiments, a physical prototype using in-kind detectors to demonstrate the feasibility of maneuverable geometry with arbitrary discrete scanning trajectory is described herein. For example, a compact prototype detector was built and the tracking mechanism using a MicroScribe device was used. An image reconstruction algorithm was implemented on a GPU device to demonstrate feasibility of near real time imaging under slow panel motion. An experiment including scanning a point source for 25 minutes and reconstructed the images in the order of a few seconds was performed using the prototype.

According to various exemplary embodiments, a simulation of a PoC-PET scanner using industrial standard Monte Carlo simulation package to study the feasibility in human scale geometry and in situations similar to clinical environment is described herein. The initial results from this simulation study illustrate how the performance of such kind of system is affected by system parameters such as detector timing resolution, number of detectors, number of scanning angles, number of scanning time and the contrast ratio of target to background. This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art.

Such other examples are intended to be within the scope of the claims if they have structural elements that do not differ from the literal language of the claims, or if they include equivalent structural elements with insubstantial differences from the literal languages of the claims.

When introducing elements of the present invention or the embodiment(s) thereof, the articles "a", "an", "the" and "said" are intended to mean that there are one or more of the elements. The terms "comprising", "including" and "having" are intended to be inclusive and mean that there may be additional elements other than the listed elements.

Approximating language, as used herein throughout the specification and claims, may be applied to modify any quantitative representation that could permissibly vary without resulting in a change in the basic function to which it is related. Accordingly, a value modified by a term or terms, such as "about," "approximately," and "substantially," is not to be limited to the precise value specified. In at least some instances, the approximating language may correspond to the precision of an instrument for measuring the value. Here and throughout the specification and claims, range limitations may be combined and/or interchanged; such ranges are identified and include all the sub-ranges contained therein unless context or language indicates otherwise.

As various changes could be made in the above without departing from the scope of the invention, it is intended that all matter contained in the above description and shown in the accompanying drawings shall be interpreted as illustrative and not in a limiting sense.

What is claimed is:

1. A positron emission tomography (PET) system comprising:
    a first detector panel including a first array of detectors; a second detector panel including a second array of detectors, said second detector panel being moveable relative to a point between said first detector panel and said second panel detector;
    a tracking system configured to detect a position of said second detector panel while imaging a subject, said tracking system comprising at least one of an articulated arm, an optical sensor, a robotic arm, an actuatable arm; and
    a computing device in communication with said first detector panel, said second detector panel, and said tracking system, said computing device configured to:
    a) receive coincidence data from said first and second detector panels, each coincidence datum received in substantially real-time;
    b) receive position data in substantially real-time from said tracking system, wherein each coincidence datum of the received coincidence data is associated with a unique position datum of the received position data;
    c) reconstruct a plurality of images throughout data acquisition based on the received coincidence data and the received position data in substantially real-time as each coincidence datum and associated position datum is received, the plurality of images comprising previous images acquired before an adjustment of a detector configuration of at least one of the first detector panel and the second detector panel and an updated image, wherein the updated image is reconstructed in substantially real-time based on the previous images and additional coincidence data and additional position data received subsequent to reconstructing the previous image;
    d) display each updated image to an operator continuously throughout data acquisition in substantially real-time;
    e) receive additional instructions from the operator based on the display for dynamically adjusting operation of the PET system using the plurality of images throughout data acquisition as substantially real-time feedback;
    f) dynamically adjust the detector configuration of at least one of the first detector panel and the second detector panel a plurality of times based at least in part on the additional instructions throughout data acquisition in substantially real-time;
    repeat a)-f) until a task requirement is satisfied; and
    output the updated image as a final image that is based on all of the previous images and additional coincidence data and additional position data received up to a time point of outputting the final image.

2. The PET system of claim 1, wherein said computing device is further configured to reconstruct the plurality of images throughout the data acquisition, wherein the updated image is reconstructed by:
    combining the previous images and additional coincidence data and additional position data received subsequent to reconstructing the previous image into combined data; and
    reconstructing the updated image from the combined the combined data.

3. The PET system of claim 1, wherein said computing device is configured to render a three dimensional (3D) image based on the plurality of reconstructed images.

4. The PET system of claim 1, wherein said tracking system is further configured to dynamically move said first detector panel and said second detector panel synchronously relative to a center of rotation.

5. The PET system of claim 1, wherein said tracking system is further configured to dynamically move said first and second detector panels synchronously relative to said point.

6. The PET system of claim 1, wherein said computing device is further configured to:
    continuously receive the position data in substantially real time from said tracking system; and
    continuously reconstruct the plurality of images throughout the data acquisition.

7. The PET system of claim 1, wherein said computing device is configured to instruct a system operator where to move the first or the second detector panel.

8. The PET system of claim 1, wherein each detector of the first and second arrays of detectors comprise gamma ray detectors capable of providing time-of-flight (TOF) information.

9. The PET system of claim 8, wherein said computing device is configured to reconstruct the plurality of images based on the received coincidence data, the received position data, and the TOF information.

10. The PET system of claim 1, further comprising a transducer and a sensor, each of which has a location and an orientation that is tracked by said tracking system, wherein said transducer and said sensor produce data for reconstruction by the said computing device to create a second modality of images.

11. The PET system of claim 10, wherein said transducer comprises at least one of an x-ray generator, an ultrasound transducer, and a laser source, and said sensor comprises at least one of an x-ray detector, an ultrasound detector, and a light sensor.

12. The PET system of claim 1, further comprising a patient tracking system to track patient motion relative to said first and second detector panels to generate patient motion information, said patient motion information used by said computing device to limit blurring and motion artifacts in reconstructed images.

13. A method for performing positron emission tomography (PET) using a PET system, said method comprising:
receiving coincidence data from a first detector panel and a second detector panel in substantially real-time, the second detector panel being movable relative to a point between the first detector panel and the second detector panel;
receiving positioning data from a tracking system in substantially real-time, the tracking system configured to detect a position of the second detector panel relative to the first detector panel while imaging a subject, wherein each coincidence data of the received coincidence data is associated with a unique position datum of the received position data;
reconstructing a plurality of images throughout data acquisition based on the received coincidence data and the received position data in substantially real-time as each coincidence datum and associated position datum is received, the plurality of images comprising a previous image and an updated image, wherein the updated image is reconstructed in substantially real-time based on the previous image and additional coincidence data and additional position data received subsequent to reconstructing the previous image;
displaying each updated image to an operator continuously throughout data acquisition in substantially real-time;
receiving additional instructions from the operator based on the display for dynamically adjusting operation of the PET system using the plurality of images throughout data acquisition as substantial real-time feedback;
dynamically adjusting a detector configuration of at least one of the first detector panel and the second detector panel a plurality of times based at least in part on the additional instructions throughout data acquisition in substantially real-time; and
repeating receiving coincidence data, receiving positioning data, reconstructing a plurality of images, displaying each updated image, receiving additional instructions, and dynamically adjusting a detector configuration until a task requirement is satisfied.

14. The method of claim 13, wherein dynamically adjusting further comprises dynamically moving the first detector panel and the second detector panel synchronously relative to a center of rotation.

15. The method of claim 13, wherein dynamically adjusting further comprises dynamically moving the first detector panel and the second detector panel synchronously relative to the point.

16. The method of claim 13, wherein:
receiving positioning data further comprises continuously receive the positioning data in substantially real time from the tracking system; and
reconstructing a plurality of images further comprises continuously reconstruct the plurality of images throughout the data acquisition.

17. The method of claim 13, wherein:
receiving coincidence data from the first detector panel and the second detector panel further comprises receiving time of flight (TOF) information from at least one of the first detector panel and the second detector panel; and
reconstructing the plurality of images further comprises reconstructing the plurality of images based on the received coincidence data, the received position data, and the TOF information.

18. The method of claim 13, wherein reconstructing the plurality of images further comprises:
receiving patient motion information from a patient tracking system, the patient tracking system configured to track patient motion relative to the first and second detector panels, wherein the patient motion information is used to limit blurring and motion artifacts in the reconstructed images.

19. The method of claim 13, wherein
reconstructing a plurality of images further comprises:
reconstructing the updated image by:
combining the previous images and additional coincidence data and additional position data received subsequent to reconstructing the previous image into combined data; and
reconstructing the updated image from the combined data.

20. The PET system of claim 1, wherein said computing device is configured to dynamically adjust operation of the PET system via the operator to execute one of:
dynamically adjusting at least one of an imaging protocol and a detector configuration if an image quality of the updated image is considered unusable by the operator; and
halting data acquisition if the image quality of the updated image is considered usable by the operator.

* * * * *